United States Patent [19]

Heywang et al.

[11] Patent Number: 6,140,507
[45] Date of Patent: Oct. 31, 2000

[54] METHOD FOR DEBENZYLATION OF DIBENZYLBIOTIN

[75] Inventors: Ulrich Heywang, Darmstadt, Germany; Heinrich Bollinger, Beringen; Hans-Rudolf Müller, Schaffhausen, both of Switzerland

[73] Assignee: Merck Patent Gesellschaft mit, Germany

[21] Appl. No.: 09/381,907

[22] PCT Filed: Mar. 17, 1998

[86] PCT No.: PCT/EP98/01545

§ 371 Date: Dec. 13, 1999

§ 102(e) Date: Dec. 13, 1999

[87] PCT Pub. No.: WO98/43979

PCT Pub. Date: Oct. 8, 1998

[30] Foreign Application Priority Data

Mar. 27, 1997 [DE] Germany ............................ 197 12 952

[51] Int. Cl.[7] .................................................. C07D 495/04
[52] U.S. Cl. ............................................................ 548/303.7
[58] Field of Search ........................................... 548/303.7

[56] References Cited

U.S. PATENT DOCUMENTS 4,537,973  8/1985  Takahashi et al. ...................... 548/303

FOREIGN PATENT DOCUMENTS 0 564 723 A1  10/1993  European Pat. Off. .
084377  10/1993  European Pat. Off. .
564723  10/1993  European Pat. Off. .

*Primary Examiner*—Laura L. Stockton
*Attorney, Agent, or Firm*—Millen, White, Zelano & Branigan, P.C.

[57] ABSTRACT

The present invention relates to a novel process for the selective debenzylation of dibenzylbiotin, which is formed as an intermediate in the synthesis of biotin, but is usually not isolated.

10 Claims, No Drawings

METHOD FOR DEBENZYLATION OF DIBENZYLBIOTIN

This application is a 371 of PCT/EP98/01545 filed Mar. 17, 1998.

The present invention relates to a novel process for the selective debenzylation of dibenzylbiotin, which is formed as an intermediate in the synthesis of biotin, but is usually not isolated.

D-(+)-biotin is prepared in a multistep process, usually by Gerecke variants, as described by Gerecke, Zimmermann and Aschwanden in Helv. Chim. Acta 53 (1970) 991 ff. A common feature of all these methods is that at the end of the synthesis dibenzylbiotin (formula (I)) is formed, but is frequently not isolated.

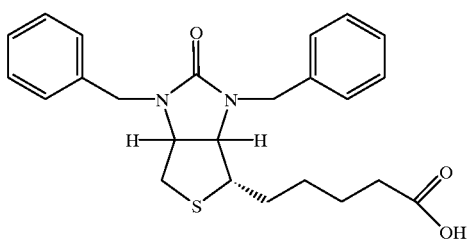

(I)

The removal of the benzyl groups has hitherto only been possible in a complex multistep process. U.S. Pat. No. 4537973 discloses debenzylation reactions using methanesulfonic acids, but these can only be used on a bench scale. Corresponding reactions with sodium amalgam are no longer permissible for environmental protection reasons. This reaction is therefore carried out, in particular on a large industrial scale, virtually exclusively using hydrobromic acid, in exceptional cases also with hydroiodic acid. However, the latter cannot be carried out on a large industrial scale for cost reasons.

Although reactions with hydrobromic acid give yields of about 90% of theory, they have, however, severe disadvantages. These include, besides the high price of the hydrobromic acid, long reaction times of from 24 to 36 hours, during which the temperature must be kept at 145° C., also the formation of lachrymatory benzyl bromide, which must either be purified for further dibenzylbiotin which can be carried out in a simile manner, at low temperatures and with a shortened reaction duration using inexpensive reagents, giving high yields of D-(+)-biotin of high purity.

The object is achieved by a process for the preparation of D-(+)-biotin by selective removal of benzyl groups by
a) adding a mineral acid to an aqueous solution of the dibenzylbiotin formed as intermediate,
b) extracting undesired by-products and cleavage products with the aid of an organic solvent after a neutral to alkaline pH has been established, and
c) crystallizing-out the liberated D-(+)-biotin by establishing an acidic pH and reducing the temperature, and separating the D-(+)-biotin off.

In this process, it is advantageous according to the invention to use impure dibenzylbiotin obtained, for example, as intermediate in the process described by DE-A1-4411101. The residue obtained after removal of the hydrogenation catalyst and removal of the solvent by distillation can be employed directly in the novel process described here.

The mineral acid used can be an acid from the group consisting of sulfuric acid and nitric acid, in particular sulfuric acid. The latter is used, in particular, as 70 to 80% sulfuric acid.

The novel process is characterized in that the mineral acid is added at a temperature of from 25 to 115° C.

This process can be carried out by, after the reaction is complete, extracting undesired by-products and cleavage products with the aid of a suitable organic solvent from group consisting of toluene and xylene after a neutral to alkaline pH has been established, and, when the solvent extraction is complete, adjusting the pH to weakly acidic, in particular to a pH of 6, and treating the aqueous D-(+)-biotin-containing solution with active carbon. The D-(+)-biotin liberated can subsequently be crystallized out after the novel process after adjustment of the pH to a value of 1–2 by cooling the reaction solution, and then separated off.

It has been found by experiments that debenzylation of dibenzylbiotin can be carried out using inexpensive 70 to 80% sulfuric acid instead of expensive hydrobromic acid. Surprisingly, the removal of the benzyl groups proceeds without attack on the carbonyl groups. This advantageously allows omission of the phosgenation step after the debenzylation. In a fairly short reaction time of only 2 to 4 hours, the reaction proceeds at a temperature of from 105 to 125° C. Lachrymatory substances are not formed, since no bromination of the departing benzyl groups can take place.

Furthermore, work-up of the D-(+)-biotin is much simpler than after debenzylation using hydrogen bromide:

After the debenzylation, a suitable organic solvent, such as, for example, xylene or toluene, is added to the reaction mixture. The pH of the solution is adjusted to between neutral and alkaline. This can be carried out by adding a base from the group consisting of NaOH and KOH in the form of a dilute aqueous solution. After phase separation and further extraction of the organic phase with a basic solution, the pH of the aqueous phase is adjusted to about 5.5 to 6.0. This solution is subsequently treated with active carbon. The pH is then slowly reduced to 1.3 with the aid of sulfuric acid at a temperature of about 80° C., and the resultant solution is slowly lowered to a temperature of 5° C., and the D-(+)-biotin is crystallized out.

In this way, D-(+)-biotin is obtained in a purity of 99%, which corresponds approximately to food quality. The purity can be further increased by recrystallization.

The examples below are given to further explain the novel process, but are not suitable for restricting the present invention to the parameters given in the examples.

EXAMPLES

Comparative Example

Preparation of biotin from dibenzylbiotin using hydrobromic acid:

320 g of crude dibenzylbiotin (containing about 80% of pure dibenzylbiotin, 0.6 mol) are mixed with 1200 g of 40% hydrobromic acid, and the mixture is refluxed for 48 hours. The benzyl bromide formed during this time (about 200 g) is removed as the lower phase using a water separator. The excess hydrobromic acid is then distilled off. The residue is taken up in 1 l of water and 300 ml of xylene, and the solution is heated to about 90° C. A pH of 9 is then established using sodium hydroxide solution, and the phases are separated. The aqueous phase is evaporated to half, and a pH of 12 is established using sodium hydroxide solution. The apparatus is then evacuated. While the pH is kept constant at 12, 130 g of phosgene are slowly blown into the evacuated apparatus at 30° C. When the reaction is complete, the vacuum is broken, and the pH is reduced to 7.0 using nitric acid or sulfuric acid. 5 g of active carbon are added, the batch is subjected to a polishing filtration and heated to 80° C., and the pH is slowly reduced to 1.5 using nitric acid (or sulfuric acid). After the mixture has been cooled overnight, the precipitated biotin is filtered off with suction and dried, giving 135 g of biotin (content: about 93%, corresponding to 125 g of pure biotin=0.51 mol, 85% of theory).

Example 1

Preparation of biotin from dibenzylbiotin using sulfuric acid:

320 g of crude dibenzylbiotin (containing about 80% of pure dibenzylbiotin, 0.60 mol) are mixed with 125 g of water, and 500 g of sulfuric acid are carefully added with stirring at such a rate that the temperature of the batch does not exceed 115° C. Stirring is then continued at 115° C. for 3 hours. 2.5 l of xylene are added, and the mixture is then firstly neutralized using 5 l of 9% sodium hydroxide solution and then rendered alkaline. The aqueous phase is separated off. The xylene phase is extracted twice more with 0.5 l of 9% sodium hydroxide solution in each case. The aqueous phase and the sodium hydroxide phases from the post-reactions are combined and adjusted to a pH of 6 at 80° C. using sulfuric acid. 12 g of activated carbon are added, the mixture is subjected to a polishing filtration, and the pH is slowly reduced to 1.5 using sulfuric acid. After the mixture has been cooled overnight, the precipitated biotin is filtered off with suction and dried, giving 128 g of biotin (content: about 99%, corresponding to 126 g of pure biotin=0.52 mol, 86% of theory).

What is claimed is:

1. In a process for the preparation of D-(+)-biotin comprising selective removal of benzyl groups from dibenzylbiotin, the improvement comprising:

a) adding water to dibenzylbiotin formed as intermediate and adding sulfuric acid, b) extracting undesired by-products and cleavage products with the aid of an organic solvent after an alkaline pH has been established, and c) crystallizing-out the liberated D-(+)-biotin by establishing an acidic pH and reducing the temperature.

2. The process according to claim 1, wherein the dibenzylbiotin is impure.

3. The process according to claim 1, wherein 70 to 80% sulfuric acid is used.

4. The process according to claim 1, wherein the organic solvent in b) is toluene or xylene.

5. The process according to claim 1, further comprising, when the solvent extraction is complete, adjusting the pH to weakly acidic, and treating the aqueous D-(+)-biotin-containing solution with active carbon.

6. The process according to claim 5, wherein the pH is adjusted to 6.

7. The process according to claim 1, wherein, in step c), the pH is adjusted to 1 to 2.

8. A process for the preparation of D-(+) biotin comprising selective removal of benzyl groups from dibenzylbiotin, comprising crystallizing D-(+) biotin from a mixture produced by extraction of undesired by-products from a mixture produced by adding water and sulfuric acid to said dibenzylbiotin.

9. The process according to claim 1, wherein the sulfuric is added at a temperature of 25to 115° C.

10. The process according to claim 1, further comprising d) separating off the D-(+)-biotin.

* * * * *